US009149186B2

(12) United States Patent
Grayzel et al.

(10) Patent No.: US 9,149,186 B2
(45) Date of Patent: Oct. 6, 2015

(54) CONFIGURATION OF CABLES FOR MONITORING SYSTEMS

(76) Inventors: Joseph Grayzel, Englewood, NJ (US); Jeffrey Grayzel, Morristown, NJ (US)

( * ) Notice: Subject to any disclaimer, the term of this patent is extended or adjusted under 35 U.S.C. 154(b) by 24 days.

(21) Appl. No.: 13/337,034

(22) Filed: Dec. 23, 2011

(65) Prior Publication Data

US 2012/0165621 A1    Jun. 28, 2012

Related U.S. Application Data

(60) Provisional application No. 61/426,806, filed on Dec. 23, 2010.

(51) Int. Cl.
*A61B 5/00* (2006.01)
*A61B 5/0428* (2006.01)
*A61B 5/0205* (2006.01)
*A61B 5/021* (2006.01)

(52) U.S. Cl.
CPC .............. *A61B 5/00* (2013.01); *A61B 5/04286* (2013.01); *A61B 5/021* (2013.01); *A61B 5/02055* (2013.01); *A61B 2562/221* (2013.01); *A61B 2562/225* (2013.01); *A61B 2562/247* (2013.01)

(58) Field of Classification Search
CPC .......................... A61B 2562/221; A61B 5/0205
See application file for complete search history.

(56) References Cited

U.S. PATENT DOCUMENTS

| | | | | |
|---|---|---|---|---|
| 3,492,987 A * | 2/1970 | Parker | | 600/21 |
| 4,224,936 A * | 9/1980 | Cox | | 600/21 |
| 4,280,507 A * | 7/1981 | Rosenberg | | 600/508 |
| 4,353,372 A * | 10/1982 | Ayer | | 600/393 |
| 4,367,728 A * | 1/1983 | Mutke | | 600/21 |
| 4,485,806 A * | 12/1984 | Akers | | 600/21 |
| 4,768,241 A * | 9/1988 | Beney | | 5/600 |
| 4,981,139 A * | 1/1991 | Pfohl | | 600/484 |
| 5,131,854 A * | 7/1992 | Jose et al. | | 439/86 |
| 5,491,299 A * | 2/1996 | Naylor et al. | | 174/36 |
| 5,626,151 A * | 5/1997 | Linden | | 128/897 |
| 5,950,625 A * | 9/1999 | Bongiovanni et al. | | 128/845 |
| 5,975,081 A * | 11/1999 | Hood et al. | | 128/845 |
| 6,247,963 B1* | 6/2001 | Rattner | | 439/502 |
| 6,833,506 B2* | 12/2004 | Wechsler | | 174/113 R |
| 6,870,109 B1* | 3/2005 | Villarreal | | 174/102 R |

(Continued)

OTHER PUBLICATIONS

Siegel JD, Rhinehart E, Jackson M, Chiarello L, and the Healthcare Infection Control Practices Advisory Committee, "2007 Guideline for Isolation Precautions: Preventing Transmission of Infectious Agents in Healthcare Settings", p. 1-225.*

*Primary Examiner* — William Thomson
*Assistant Examiner* — Marie Archer

(57) ABSTRACT

A physical configuration of cables connecting a monitoring apparatus to a human patient, where said patient and his immediate surroundings define a potentially infectious contaminated zone. The configuration provides for the monitor and main trunk cable to lie outside of the contamination zone, and one or more serial cables connect to the trunk cable and enter the contamination zone to provide contact with the patient. This physical configuration prevents contamination of the monitor and trunk cable, so they may be reused on successive patients, while lightweight and inexpensive serial cables contacting the patient and his contamination zone may be disposable. Examples of monitoring various physiological variables are provided to exemplify the universal concept of such physical configuration. Adaptation for wireless transmission is also described.

25 Claims, 10 Drawing Sheets

(56) References Cited

U.S. PATENT DOCUMENTS

| | | | |
|---|---|---|---|
| 6,971,985 B2* | 12/2005 | Perlatti | 600/21 |
| 7,521,634 B2* | 4/2009 | Clem et al. | 174/113 R |
| 8,070,508 B2* | 12/2011 | Flagler | 439/470 |
| 8,076,580 B2* | 12/2011 | Kolasa et al. | 174/105 R |
| 8,089,001 B2* | 1/2012 | Wang | 174/110 R |
| 8,375,572 B2* | 2/2013 | Lind et al. | 29/825 |
| 2004/0074212 A1* | 4/2004 | Yachi et al. | 55/385.2 |
| 2006/0178030 A1* | 8/2006 | Lund et al. | 439/287 |
| 2006/0247487 A1* | 11/2006 | Arts et al. | 600/21 |
| 2007/0056593 A1* | 3/2007 | Kubicsko et al. | 128/846 |
| 2007/0156005 A1* | 7/2007 | Baum | 588/249 |
| 2007/0260133 A1* | 11/2007 | Meyer | 600/393 |
| 2012/0071740 A1* | 3/2012 | Kaestle | 600/323 |

\* cited by examiner

CONFIGURATION OF CABLES FOR MONITORING SYSTEMS

RELATED APPLICATIONS

This application claims the benefit of U.S. Provisional Application No. 61/426,806 filed Dec. 23, 2010

FIELD

The invention generally relates to apparatus and configurations of apparatus for use in patient monitoring systems.

BACKGROUND

Ill patients require surveillance of essential information relating to the patient's condition. Such information may relate to physiologic or anatomic functions or status. Apparatus which perform this surveillance function are referred to as monitoring systems. The most common signal employed for continuous surveillance is the electrocardiogram (ECG). Other physiologic functions that can be monitored include, but are not limited to temperature, blood pressure, respiration, blood oximetry, cardiac bio-impedance, and others. The system comprises an electronic monitor console connected to one or more cables, which terminate with a sensor device interfaced with the patient.

The most common location for the electronic monitor console is at the patient's bedside, but the patient may reside on a reclining chair, stretcher, gurney, operating-room table, or other similar modality, with the electronic monitor console similarly nearby. Often the patient can reach out and touch the electronic monitor console. One or more cables connect the electronic console to the patient to convey information from the patient. Such cables are most often electrical/electronic lines, but may also be pneumatic, hydraulic, or fiber-optic, consistent with the information being conveyed from patient to electronic console. Henceforth, in the description below, the term cable shall be broadly defined as the means of conveying such signals from the patient to the monitor console. Thus, the term cable could mean an electrical cable, a pneumatic cable, a fiber-optic cable, or other, depending on the application.

The modality that will be employed as the paradigm for initial description of a system configuration is the ECG, followed by analogous applications to temperature and blood pressure. The ECG is a wave-form depicting the time-varying difference in electrical potential between two points on the surface of the skin. Electrical connection to the skin is provided by a conductive electrode connected to a conductive wire; the simplest arrangement consists of the two active electrodes whose potential difference is to be measured, and a third electrode serving as a ground or reference electrode. This arrangement provides one ECG signal or lead; each additional lead requires an additional electrode with attached conductive wire. Since it is often desirable to monitor several ECG leads, it is common to have four or more electrodes with wires grouped as a packaged assembly.

To limit and control the transfer of infectious agents within the hospital environment, these electrodes with attached wires are frequently discarded after each patient use, since they are considered to be contaminated by the patient and not suitable for transfer to another ill individual. Being disposable, the electrode-wire assembly employs wires of minimal length which lie entirely on the patient or on his bed. Hereafter, we may refer to such wires as serial wires, since they are in series with the trunk cable, which then extends to the input connector of the electronic monitoring console. Thus, a bundled group of wires may constitute a cable and be denoted as the serial cable, so named as it is in series with the trunk cable. A connecting means, such as a metallic pin, located at the proximal end of each wire within the serial cable, couples to a multiple-input yoke at the distal end of a permanent trunk cable. Other connecting means may be possible. Of note, the terms proximal and distal are referenced to the electronic monitor console, proximal being closer to the console and distal being further away, in the direction of the patient.

The trunk cable extends all the way to the electronic monitor console to which it couples via a substantial multiple-conductor connector. Thus, the trunk cable contains multiple shielded wire conductors within its entire length and terminates in a multiple pin-receptive yoke at its distal end, and a substantial multiple-conductor connector at its proximal end, which is inserted into the input receptacle of the monitor console. Parenthetically, it is again noted that cables which are pneumatic, hydraulic, fiber-optic, or of a non-electronic nature will require respectively-appropriate connectors.

The trunk-cable is a relatively expensive component of the monitoring system and is not considered a disposable item, but is reused continuously through the sequence of patients to be interfaced with the monitor over time. The trunk-cable conspicuously reaches from the monitor console to the patient's bed, is contacted frequently by the patient, his bedclothes and linens, and is also handled frequently by caregivers at the patient's bedside. Thus, the trunk-cable is exposed directly to multiple sources of microbial contamination, and can transmit same to the subsequent sequence of patients for whom the monitoring system is employed.

Nosocomial infections are a major cause of in-hospital morbidity and responsible for large increases in hospital costs, for which reimbursement is not given. Hence, hospitals have intensely addressed causes of such hospital-acquired infection and have identified potential culprits. Among such sources of contamination and transmission of microbes are trunk-cables for ECG and trunk-cables for other monitored parameters, such as previously mentioned temperature, blood pressure, respiration, blood oximetry, bio-impedance, and others. Many hospitals attempt to reduce the virulence of trunk-cables by frequent wiping with anti-microbial disinfectants, but microbial cultures of trunk-cables have revealed such cleansing to be of limited value and not adequate for the objective. Hence, contamination of trunk cables remains a serious problem, contributing to the transmission of infective agents from one patient to another.

OBJECTS

It is an object of the present application to minimize or eliminate the role of trunk-cables as a discernable vehicle for the inter-patient transmission of infective agents, such as bacteria and fungi.

It is a further object of the present application to reduce hospital morbidity resulting from transmission of nosocomial infection by monitoring systems.

It is a further object of the present application to reduce hospital costs resulting from transmission of nosocomial infection by monitoring systems.

It is yet another object of the application to provide a monitoring system wherein the monitor console and trunk cable reside completely outside the infectious zone.

It is still another object of the application to provide a trunk cable of a length such that when its proximal end is attached to the monitor console, its length is insufficient to allow its distal end to reach the perimeter of the infectious zone surrounding a patient.

It is yet another object of the application to provide a serial cable that is disposable.

It is still another object of the application to provide an intermediate cable to be used when the length of the serial cable is insufficient to have its proximal end extend beyond the perimeter of the infectious zone when its distal end is coupled to the patient.

It is yet another object of the application to provide for wireless transmission of information from a transmitter located inside or outside of the infectious zone to a receiver located outside the infectious zone.

It is still another object of the application to provide a method for preventing the transfer of infective agents along a series of patients successively utilizing the same monitoring system.

SUMMARY

The present application describes spatial configurations of the monitor console and its associated cables which run from the monitor console to the patient. The patient's bed and a defined zone surrounding the bed are susceptible to contamination by the patient, and together are denoted hereafter as the Infectious Zone. The configuration described herein reduces or prevents contamination of the trunk cable, which is the expensive and reused portion among the group of cables. This is accomplished by locating the monitor console outside the infectious zone, and attaching thereto a short trunk cable whose length is not sufficient to reach the boundary of the infectious zone, thereby preventing the usual physical contact leading to contamination. The serial cable connected between the trunk cable and patient is made sufficiently long so that it extends from the trunk cable located outside the infectious zone to the patient's corpus. Thus, only the serial cable is susceptible to contamination, and it is made to be disposable and discarded. Compared to present-art cable systems, the trunk cables described herein are generally shorter than present trunk cables, and the serial cables described herein are generally longer than present-art serial cables. Both the trunk cable and the monitor console as described herein are always located outside the infectious zone.

The foregoing configuration for a monitoring system, consisting of both monitor console and trunk cable lying outside the infectious zone, and the serial cable will be described in detail for several monitoring modes, namely ECG, temperature, and blood pressure. It will then be evident to one skilled in the art the manner of applying the described system configurations to any other physiological parameter amenable to monitoring.

A second configuration is presented as follows. In the first configuration the serial cable extends from the patient to a point outside the infectious zone where it connects to the trunk cable. In the second configuration this primary serial cable remains short, not extending outside the infectious zone, and a second serial cable named the Intermediate Cable, extends from the proximal terminus of the primary serial cable to the distal end of the trunk cable lying outside of the infectious zone. This configuration enables present-day cables to remain unchanged, utilizing the existing short serial cable, while the intermediate cable continues to a point outside the infectious zone. This second configuration also accomplishes the desired result, namely avoiding contamination of the console monitor and the non-disposable trunk cable, both of which reside outside the perimeter of the infectious zone.

The first and second configurations described above may be modified by the addition of wireless transmission of the patient's physiologic signals from the patient to the monitor. A wireless transmitter may be attached to the proximal end of a short or long serial cable, or to the proximal end of an intermediate cable. Alternatively, the transmitter may be incorporated directly into the proximal end of a short or long serial cable, or to the proximal end of an intermediate cable. Alternatively, the transmitter and the sensor may be integrated, in which case neither a serial cable nor an intermediate cable is necessary. A wireless receiver may be attached to or incorporated into the distal end of the trunk cable. Alternatively, a receiver may be connected directly to the monitor or incorporated into the monitor and contained within the monitor's enclosure.

For the case where a short serial cable is employed, this arrangement does present the additional problem caused by the transmitter residing inside the infectious zone, since the transmitter is often costly and usually not treated as disposable. In the case where the transmitter will be reused, it would be advantageous for the transmitter to be enclosed within a disposable container which protects it from contamination. This is easily accomplished, for example, with a clear plastic bag-like envelope with a sealable opening, which maintains the cleanliness of the transmitter, yet permits it to be easily removed from the container or bag for subsequent use. A clear plastic material permits RF transmission, optical transmission, infra-red transmission, and other modalities through its protective envelope. Other types of containers could also be designed, including those that are more substantial, such as a plastic enclosure, and amenable to sterilization. The addition of wireless transmission may also be incorporated into other configurations described within this specification.

The configurations described above and in detail below may be advantageously applied to other monitoring systems to capture any information relating to a patient's condition that is amenable to patient monitoring.

In yet another configuration, the elimination of sequential infectious contamination by a reusable cable of a monitoring system employed among a series of patients may also be accomplished by sheathing or otherwise entirely enclosing the reusable trunk cable from its proximal to distal end in a covering, which herein will be referred to as a sheath. Such a sheath could be inexpensive and disposable after each patient use. This is advantageously accomplished by a lightweight flexible tubular structure, such as a thin-walled impermeable plastic tube or envelope, preferably transparent so that proper disposition of the cable within the plastic tube can be observed at all times. Alternatively, the sheath could be made from a polymeric film. It would be desirable that the sheath be capable of assuming a collapsed or compacted form, which can be expanded longitudinally to the full length of the trunk cable. For example, the thin-walled envelope could possess a series of radially-oriented pleats, analogous to pleats on an accordion, which would permit the envelope to be compressed into a compact structure for packaging, shipping and handling, and then be expanded longitudinally over and around the trunk cable along its full length. An alternate structure for the sheath would be a telescopic disposition of the sheath with adjacent lengths folded sequentially within one another. This structure would also be initially compact, and then expanded longitudinally to envelop the entire length of the trunk cable. A third structure, less ordered than the foregoing, would simply be a thin-walled tubular plastic film crumpled along its axis. In some configurations the sheath would extend to a point that would encompass the proximal end of the serial cable or the wireless receiver if one is being utilized. In yet other configurations the sheath may extend even further and may be of a length to reach from the monitor console to the patient.

Since it is desirable to have the trunk cable sealed and isolated within the sheath, the ends of the sheath would comprise a means to seal it around the cable or the connector. The open ends may be occluded with a partition, generally perpendicular to the long axis of the sheath. Such an occlusive end-member is advantageously composed of an elastic material, such as a latex-like rubber or a compressible sponge. The elastic end-partition would possess a central slit or puncture through which the cable could be inserted into the sheath, yet the elastic end-partition would recoil snugly around the cable in a conforming manner to provide a sufficiently tight seal around the end of the cable to prevent entry of contaminants. Other means of sealing the end of the sheath are also contemplated. To further accomplish the objective of a contaminant-free cable, the interior of the sheath could possess an antimicrobial chemical or other active substance, such as an interior coating to the sheath, or dispersion in powder form, or a liquid impregnated into the end-partition which is wiped along the cable as it is inserted into the sheath.

The foregoing configurations enable methods of reducing the transmission of infection from patient to patient amongst a series of patients successively utilizing the same monitoring system. Such methods include the steps of assessing the infectious zone and defining its perimeter; placing the monitor console outside said perimeter; attaching the proximal end of the trunk cable to the monitor console and placing the entirety of the trunk cable in a position outside of the infectious zone; connecting the trunk cable distal end to the serial cable proximal end such that both ends are positioned outside the perimeter of said infectious zone; extending the serial cable distal end into the infectious zone; coupling the sensor device located at the distal end of the serial cable to the patient; if necessary due to insufficient combined length of the trunk cable and the serial cable, attaching an intermediate cable to both the serial cable proximal end and the trunk cable distal end to complete a transmission pathway for the patient information to be transmitted from the patient to the monitor console. In yet another configuration, the intermediate cable can be replaced by a wireless transmission device. In yet another configuration, the trunk cable and/or serial cable and/or intermediate cable is encased in a sheath that is deployed over the cable, where said sheath is comprised of an impervious material constituting an effective barrier against microbial agents.

BRIEF DESCRIPTION OF THE DRAWINGS

The accompanying drawings which are incorporated in and constitute part of this specification, illustrate some, although not all, possible system configurations.

DETAILED DESCRIPTION

Figure 1:
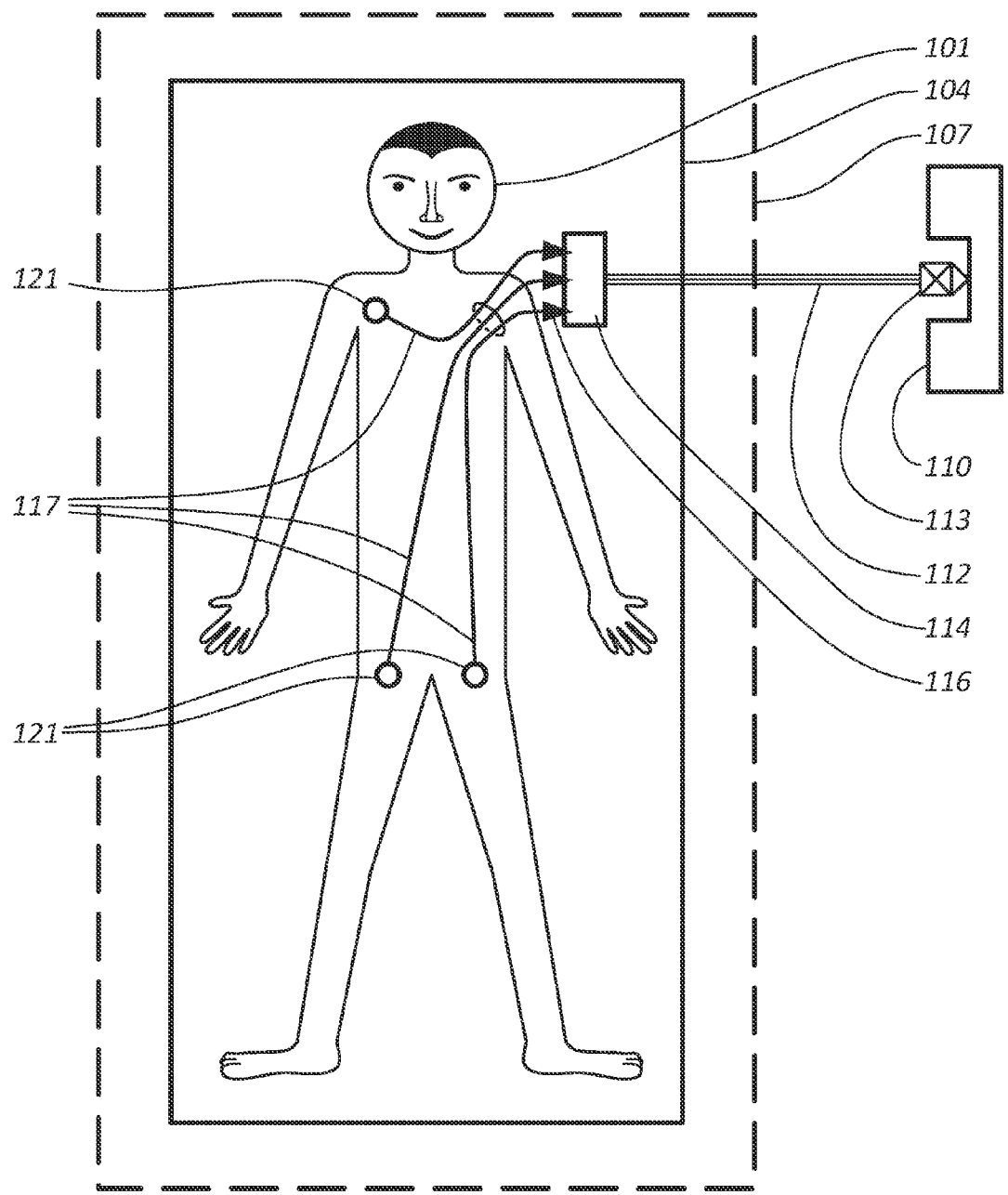
FIG. 1 depicts a present-art system configuration for ECG monitoring

FIG. 1 depicts a present-art monitoring system for the ECG. The patient 101 is shown supine on bed 104 or analogous surface for repose or transport. Outside and beyond the perimeter 104 of the bed, dashed lines 107 demarcate the outer boundary or perimeter of the infectious zone, which is beyond the patient's reach. Electronic monitor console 110 is shown outside the infectious zone, although it is frequently positioned at the patient's bedside and within reach of the patient, hence within the infectious zone. Present-art practice generally locates the monitor console according to physical constraints of the available space and operator convenience, without attention to issues of contamination by the patient. Trunk Cable 112 is shown connected to the console by connector 113 at its proximal end, and possesses a connector or yoke 114 at its distal end. Three conductive wires 117 comprise the serial cable shown herein, but more elaborate serial cables contain additional electrical wires to enable multiple ECG leads (waveforms). Each conductive wire comprising the serial cable terminates at its distal end in a conductive electrode 121 which is conductively coupled to the skin surface. Other types of conductive couplings may be used, not shown, such as subcutaneous or intravascular. The proximal end of the serial cable connects to the yoke 114 of the trunk cable, such connection shown herein by pin connectors 116, though other types of connectors may be employed. The present-art system configuration shown in FIG. 1 makes evident the ease of frequent contamination of the trunk cable and its yoke connector by the patient, bedclothes, and other personal sundries residing with the patient. The serial cable is generally disposable.

Figure 2:
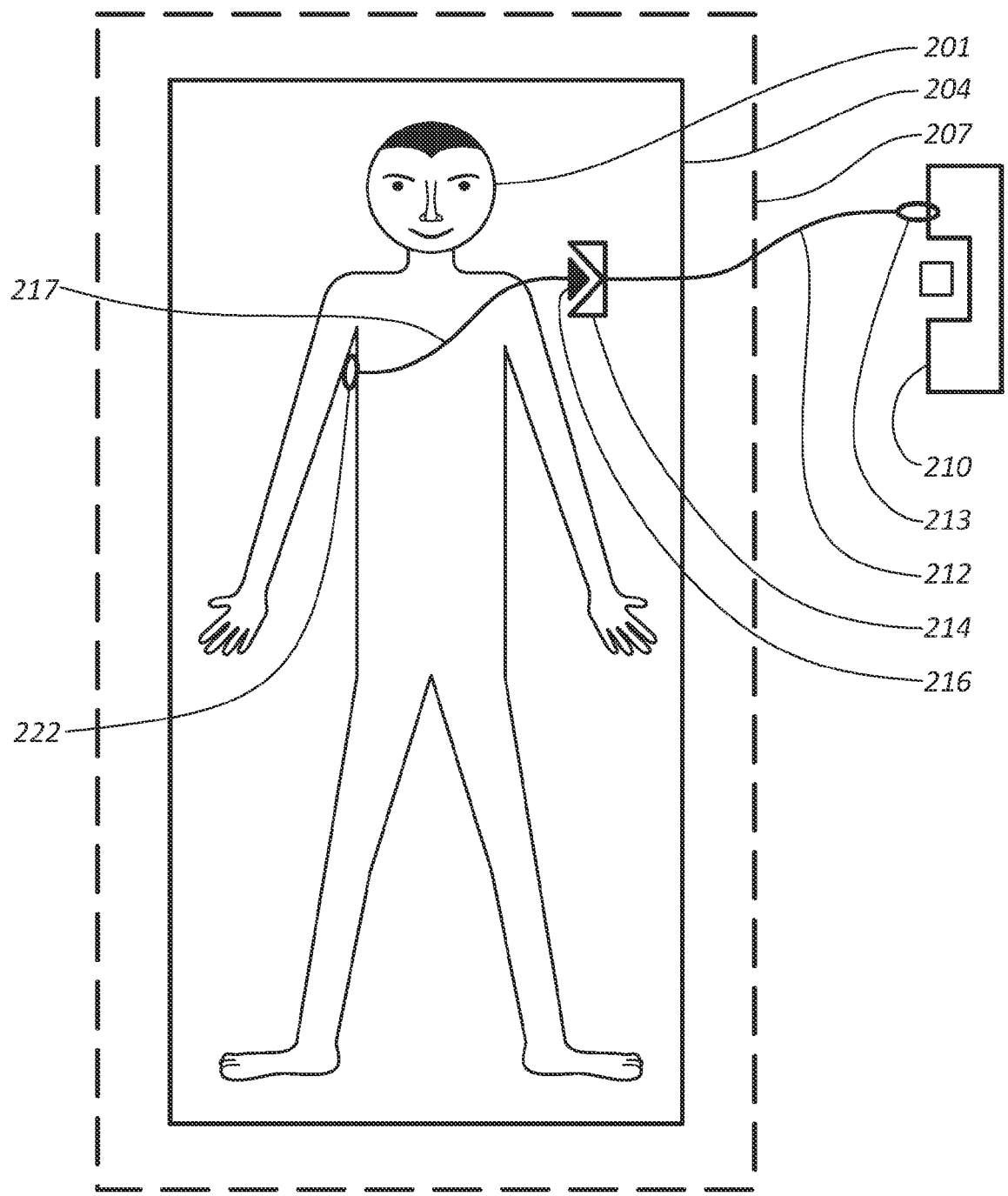
FIG. 2 depicts a present-art system configuration for temperature monitoring.

FIG. 2 depicts a present-art monitoring system for body temperature, showing the patient 201, the perimeter 204 of the bed, and the outer boundary or perimeter 207 of the infectious zone. Electronic monitor console 210 is shown outside the infectious zone and engages input connector 213 on the proximal end of the trunk cable 212. The distal end of the trunk cable possesses connector 214 which couples to connector 216 on the proximal end of serial cable 217, possessing the requisite number of conductors to convey the signal representing body temperature. The distal end of the serial cable connects to the temperature sensor 222, such as thermistor or thermocouple, shown in the axilla of the patient. FIG. 2, in a manner analogous to FIG. 1, shows the consistent contamination of the trunk cable by the patient and his intimate physical environment.

Figure 3:
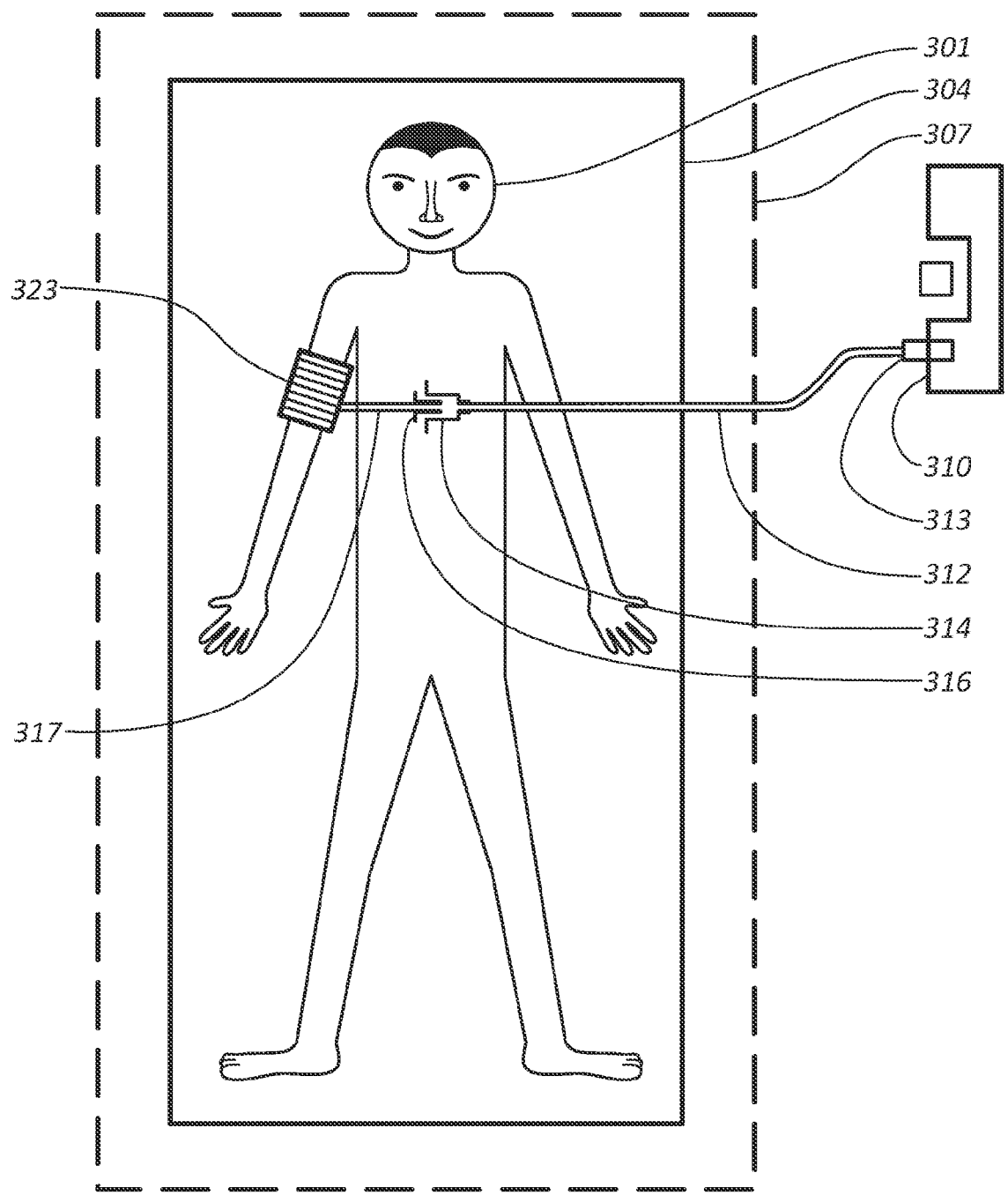
FIG. 3 depicts a present-art system configuration for blood-pressure monitoring.

FIG. 3 depicts a present-art monitoring system for non-invasive blood pressure measurement, showing the patient 301, the perimeter of the bed 304, and the perimeter 307 of the infectious zone. Electronic monitor console 310 is shown outside the infectious zone and receives pneumatic input connector 313 on the proximal end of the pneumatic trunk cable 312 (tubular trunk line). The distal end of the tubular pneumatic trunk line possesses connector 314, which couples pneumatically to connector 316 on the proximal end of the pneumatic serial cable 317, the serial tubular line to inflatable blood-pressure cuff 323. The electronic console contains an air pump to inflate the cuff, a valve to gradually bleed air from the cuff after adequate inflation, a pressure sensor to measure air pressure within the tubular lines and cuff, and algorithms for controlling the operation of the system and for computing blood pressure from the pulsating pressure fluctuations which occur during deflation of the pressurized cuff. This method is well-known to those skilled in the art, and further details are not herein provided. While disposable blood pressure cuffs are now available, but not always employed, their serial pneumatic line 317 is always short, and connector 316 lies within the infectious zone, as does its mating connector 314; the pneumatic trunk cable 312 extending to the monitor console 310 is extensively within the bed and infectious zone.

Figure 4:
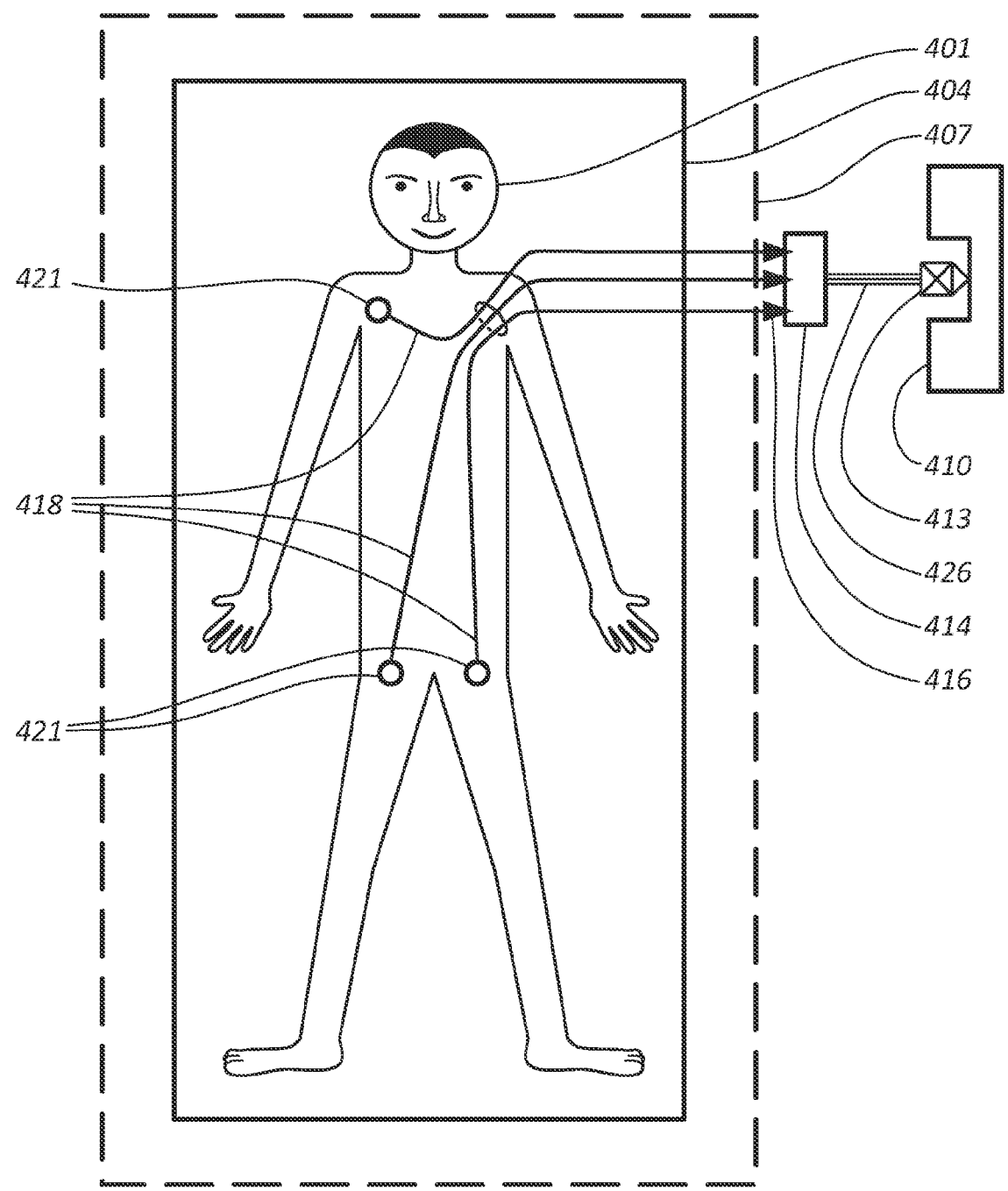
FIG. 4 depicts a configuration as applied to ECG monitoring.

FIG. 4 depicts the first configuration applied to ECG monitoring, showing the patient 401, the perimeter 404 of the bed, and the perimeter 407 of the infectious zone. Electronic monitor console 410 is located outside the infectious zone, and receives connector 413 from the proximal end of trunk cable 426. Trunk cable 426 lies entirely outside the infectious zone, as does the connector or yoke 414 at its distal end. Thus, the trunk cable is not subject to direct contamination by the patient or his intimate environment. Pin connectors 416, affixed to the proximal end of serial cable 418, also lie outside the infectious zone, but serial cable 418 enters the infectious zone and extends to the patient, where ECG electrodes 421 at the distal ends of the serial cable's wires are conductively coupled to the patient. Compared to present art as shown in FIG. 1, the configuration as drawn in FIG. 4 shows the trunk cable to be shorter and the disposable serial cable to be longer than present art.

Figure 5:
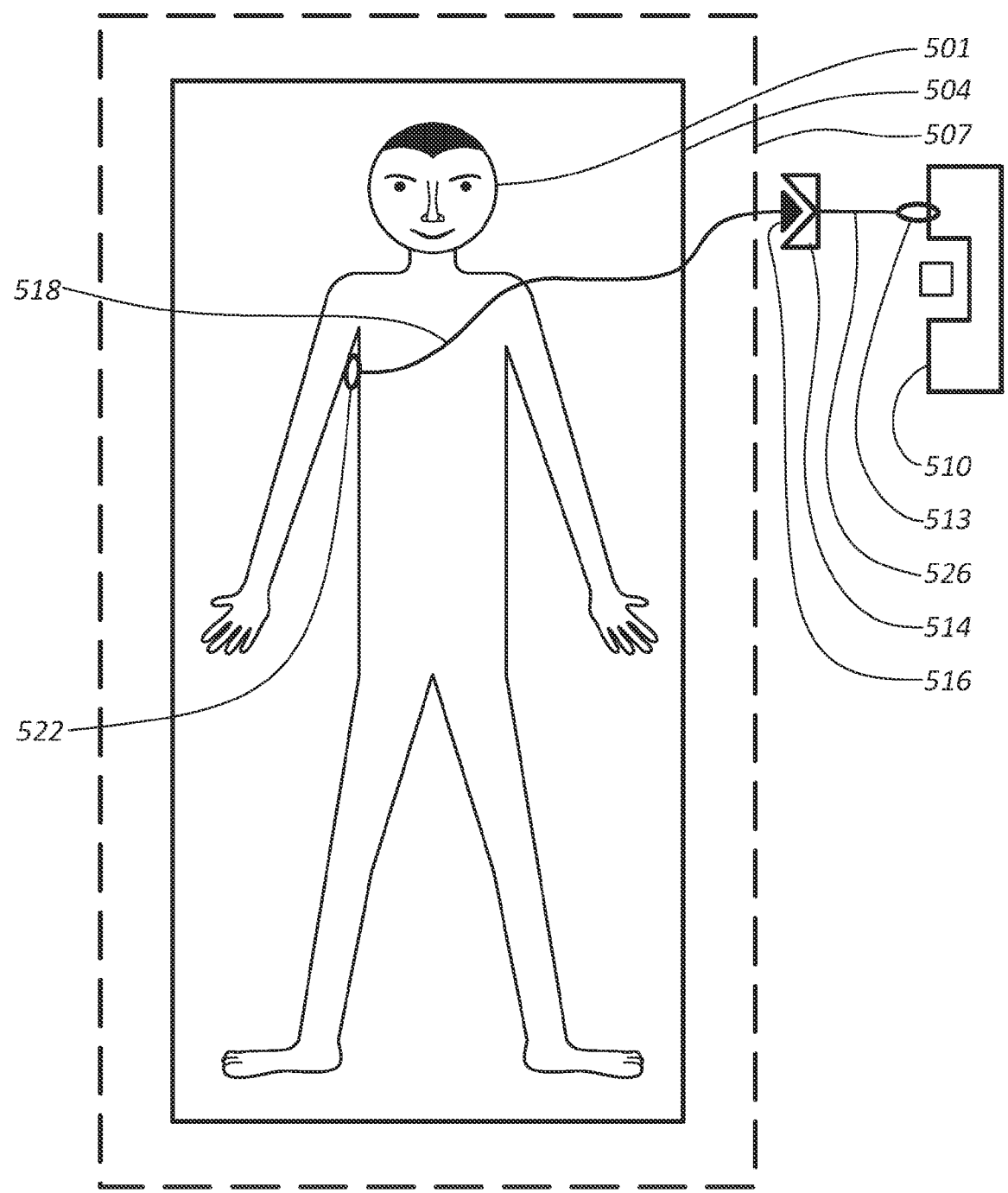
FIG. 5 depicts a configuration as applied to temperature monitoring.

FIG. 5 depicts the first configuration applied to monitoring of temperature, showing patient 501, the perimeter 504 of the bed, and the perimeter 507 of the infectious zone. Electronic monitor console 510 is located outside the infectious zone, and receives connector 513 from the proximal end of trunk cable 526. Trunk cable 526 lies entirely outside the infectious zone, as do connector 513 at its proximal end and connector 514 at its distal end. Thus, the trunk cable is not subject to direct contamination by the patient or his intimate environment. Connector 516 at the proximal end of serial cable 518 also lies outside the infectious zone, but serial cable 518 enters the infectious zone and extends to the patient, where temperature sensor 522 at the distal end resides in the patient's axilla. Compared to present art as drawn in FIG. 2, the configuration as drawn in FIG. 5 shows the trunk cable to be shorter and the disposable serial cable to be longer than present art.

Figure 6:
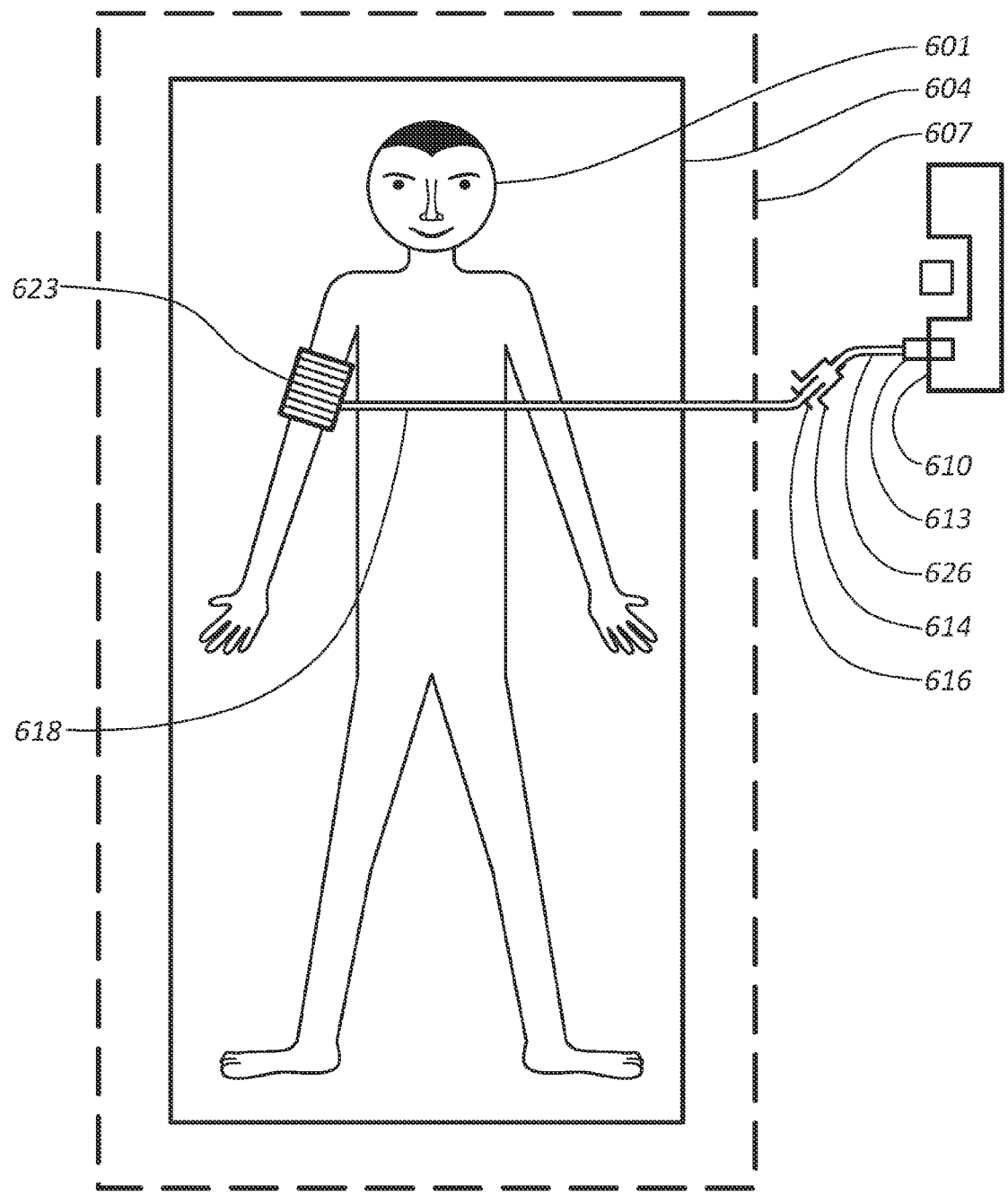
FIG. 6 depicts a configuration as applied to blood-pressure monitoring.

FIG. 6 depicts the first configuration applied to monitoring of blood pressure, showing patient 601, the perimeter 604 of the bed, and the perimeter 607 of the infectious zone. Electronic monitor console 610 is located outside the infectious zone, and receives connector 613 from the proximal end of pneumatic trunk cable 626. Trunk cable 626 lies entirely outside the infectious zone, as does pneumatic connector 614 at its distal end. Thus, pneumatic trunk cable 626 is not subject to direct contamination by the patient or his intimate environment. Pneumatic connector 616 at the proximal end of serial pneumatic cable 618 also lies outside the infectious zone; serial pneumatic cable 618 enters the infectious zone and extends to the patient, where blood-pressure cuff 623 at the distal end is wrapped around the patient's arm. Compared to present art as drawn in FIG. 3, the configuration as drawn in FIG. 6 shows the pneumatic trunk cable to be shorter and the disposable serial pneumatic cable to be longer than present art.

Figure 7:
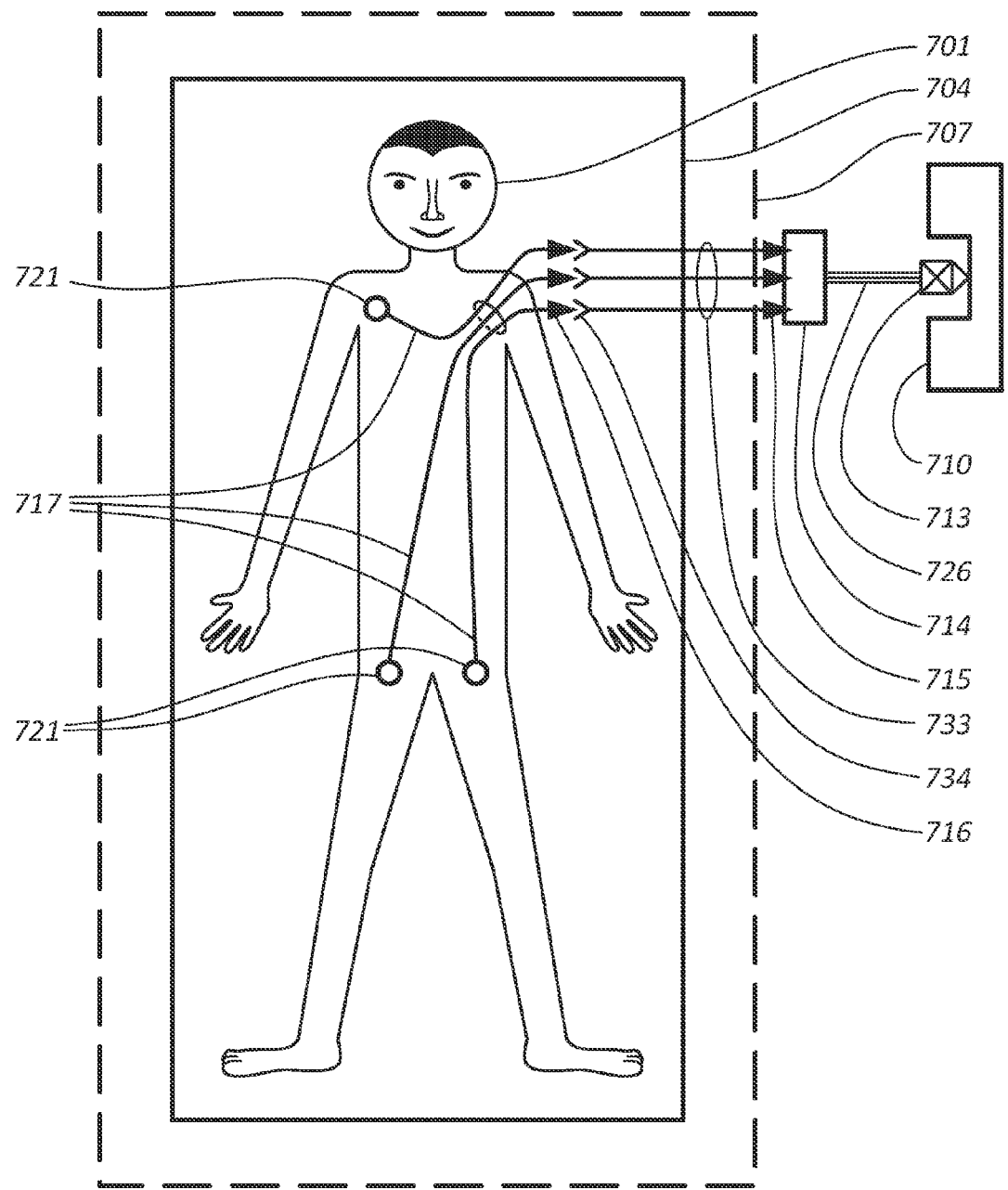
FIG. 7 depicts a configuration as applied to ECG monitoring.

FIG. 7 depicts the second configuration applied to ECG monitoring, showing patient 701, the perimeter 704 of the bed, and the perimeter 707 of the infectious zone. Electronic monitor console 710 is located outside the infectious zone, and receives connector 713 from the proximal end of trunk cable 726. Trunk cable 726 lies entirely outside the infectious zone 707, as does yoke connector 714 at its distal end. Thus, trunk cable 726 is not subject to direct contamination by the patient or his intimate environment. Pin connectors 715 are affixed to the proximal end of an intermediate cable 733, and also lie outside the infectious zone, while intermediate cable 733 enters the infectious zone and extends to the proximal end of the serial cable 717. Pin-receptive connectors 734 at the distal end of the intermediate cable mate with pin connectors 716 at the proximal end of the serial cable. The distal ends of wires comprising the serial cable terminate in conductive electrodes 721 which are conductively coupled to the patient. In this second configuration, both the serial cable and the intermediate cable are disposable. This permits use of serial cables as presently manufactured, which are not sufficiently long to reliably extend outside the infectious zone, while the intermediate cable of simple structure and inexpensive serves as an extension line for the serial cable and reaches outside the infectious zone to the yoke connector 714 of the trunk cable 726. Essentially, serial cable 717 linked to intermediate cable 733 replaces serial cable 418 of FIG. 4.

Figure 8:
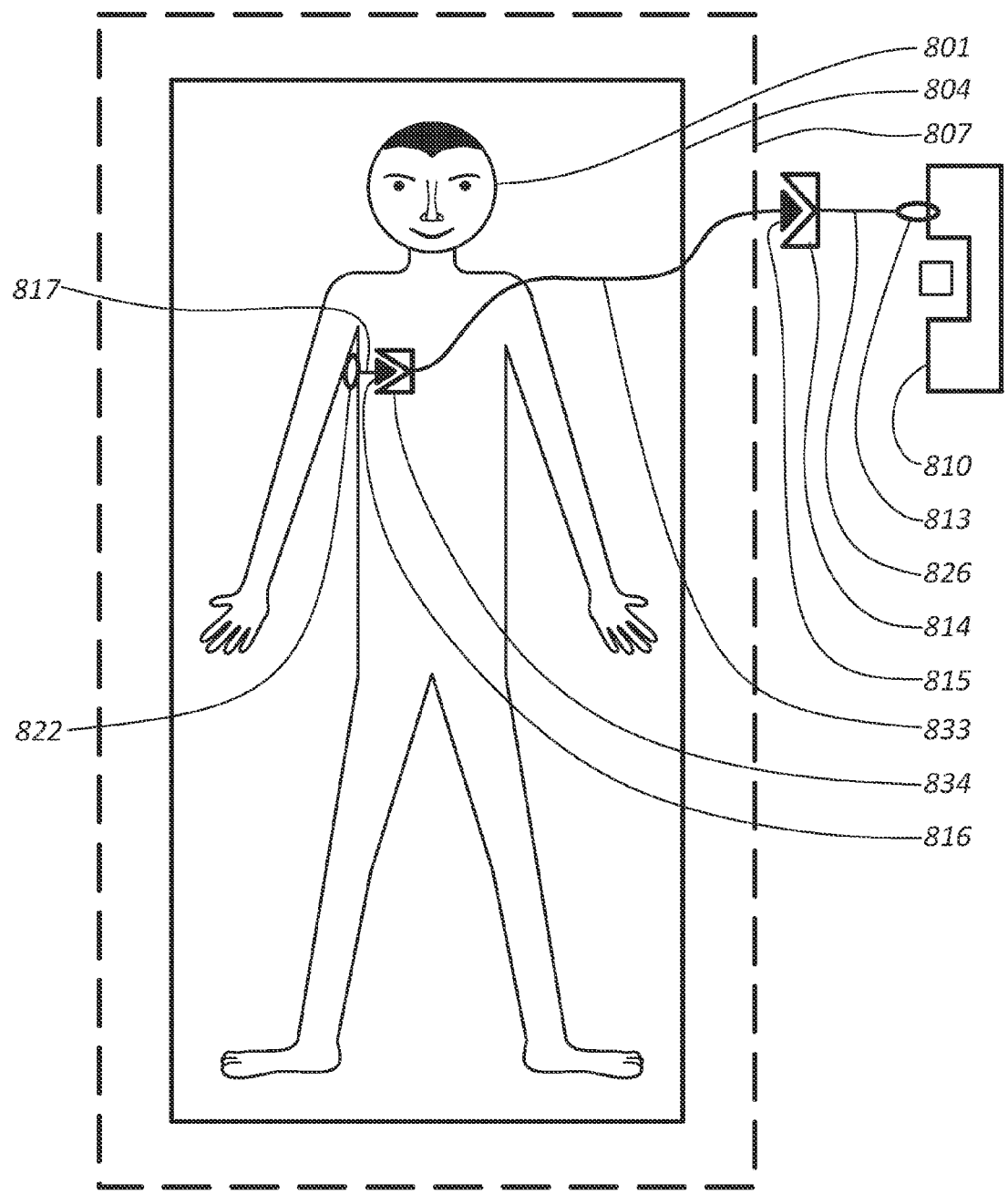
FIG. 8 depicts a configuration as applied to temperature monitoring.

FIG. 8 depicts the second configuration applied to monitoring of temperature, showing patient 801, the perimeter 804 of the bed, and the perimeter 807 of the infectious zone. Electronic monitor console 810 is located outside the infectious zone, and receives connector 813 from the proximal end of trunk cable 826. Trunk cable 826 lies entirely outside the infectious zone 807, as does connector 814 at its distal end. Thus, trunk cable 826 and its connectors are not subject to direct contamination by the patient or his intimate environment. Mating connector 815 is affixed to the proximal end of an intermediate cable 833, and also lies outside the infectious zone, while intermediate cable 833 enters the infectious zone and extends to the proximal end of the serial cable 817. At the distal end of intermediate cable 833, receptive connector 834 mates with connector 816 at the proximal end of serial cable 817. The distal end of serial cable 817 connects to the temperature sensor, which is shown nestled in the patient's axilla. In this second configuration for temperature monitoring, both serial cable 817 and intermediate cable 833 are disposable. Essentially, serial cable 817 linked to intermediate cable 833 replaces serial cable 518 of FIG. 5.

Figure 9:
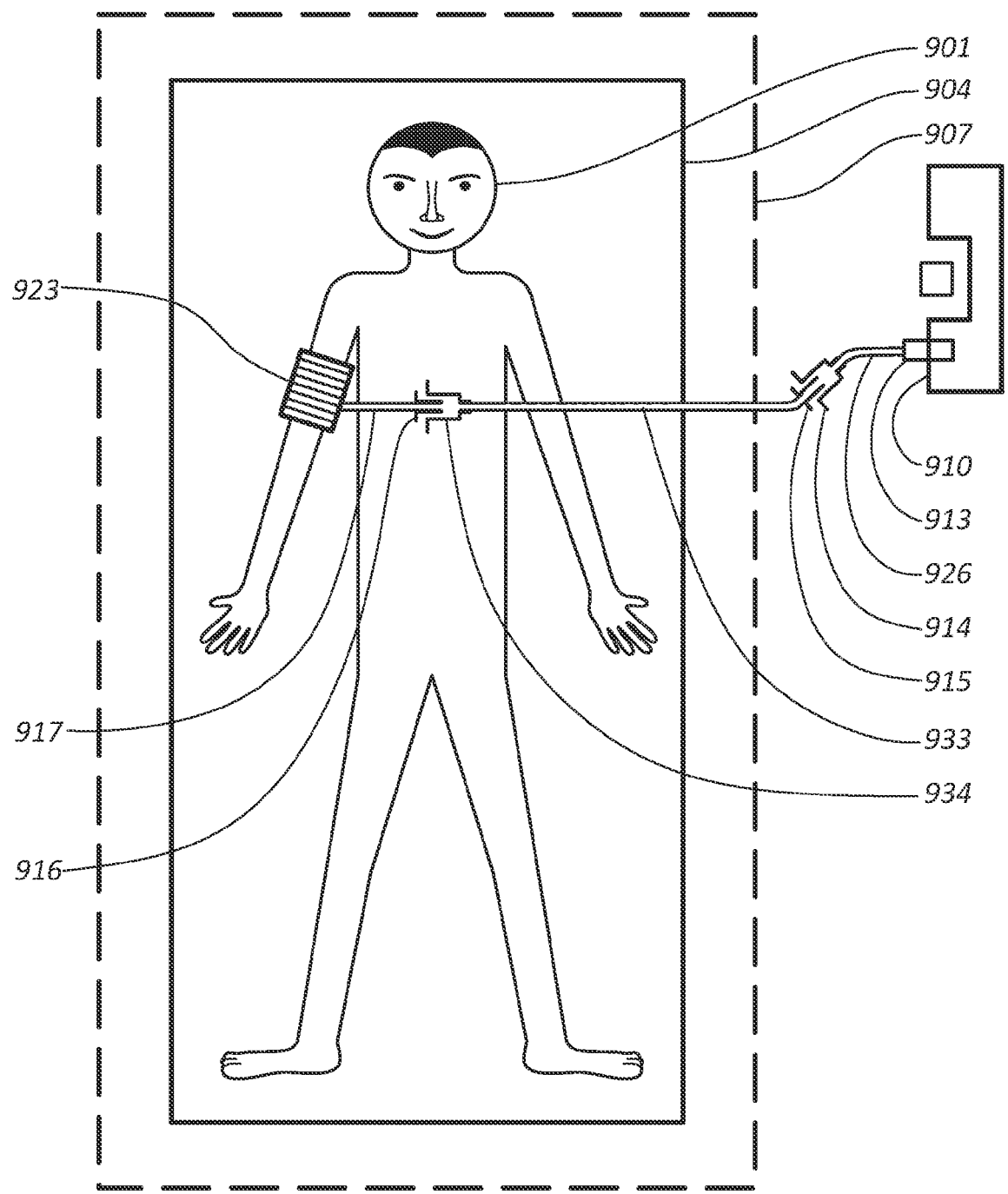
FIG. 9 depicts a configuration as applied to blood-pressure monitoring.

FIG. 9 depicts the second configuration applied to monitoring of blood pressure, showing patient 901, the perimeter 904 of the bed, and the perimeter 907 of the infectious zone. Electronic monitor console 910 is located outside the infectious zone, and receives pneumatic connector 913 from the proximal end of pneumatic trunk cable 926. Trunk cable 926 lies entirely outside the infectious zone 907, as does pneumatic connector 914 at its distal end. Thus, pneumatic trunk cable 926 and its connectors are not subject to direct contamination by the patient or his intimate environment. Mating connector 915 is affixed to the proximal end of an intermediate pneumatic cable 933, and also lies outside the infectious zone, while intermediate pneumatic cable 933 enters the infectious zone and extends to the proximal end of the serial cable 917. At the distal end of intermediate pneumatic cable 933, receptive pneumatic connector 934 mates with pneumatic connector 916 at the proximal end of serial pneumatic cable 917. The distal end of pneumatic serial cable 917 connects to the blood pressure cuff 923, which is wrapped around the patient's arm. In this second configuration for monitoring of blood pressure, both serial pneumatic cable 917 and intermediate pneumatic cable 933 are disposable. Essentially, serial pneumatic cable 917 linked to intermediate pneumatic cable 933 replaces serial pneumatic cable 618 of FIG. 6. Present-day disposable blood-pressure cuffs generally possess a short length of pneumatic cable (tubing) permanently affixed thereto, which would serve as the serial pneumatic cable 917 of the present FIG. 9.

Figure 10A:
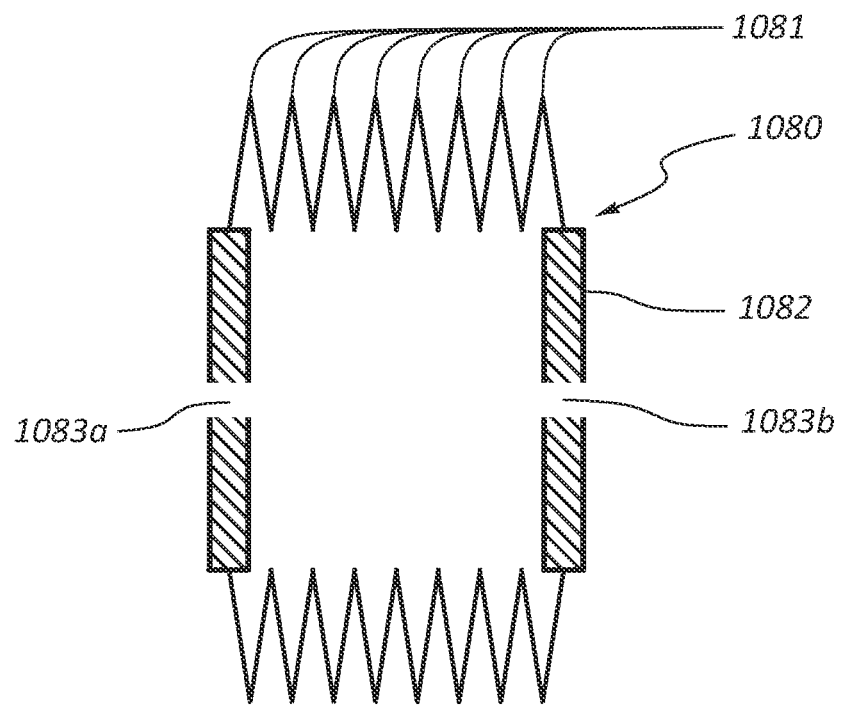
FIGS. 10A-10B depicts configurations of a sheath for encasing the cables.
Figure 10B:
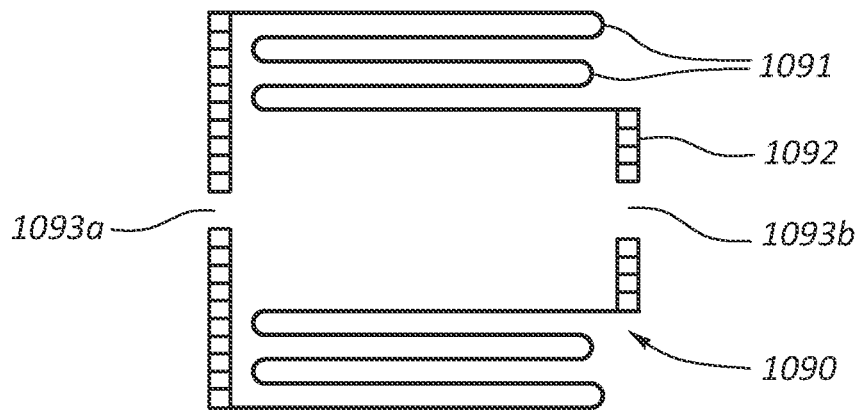

FIGS. 10A-10B depicts sheaths primarily used for encasing the trunk cable of the monitoring system, and could also be used for the other cables as well. FIG. 10A is a longitudinal section along the central axis showing an configuration having a pleated sheath with end-partitions. The pleated sheath 1080 is generally shown, with radially-oriented pleats 1081, end-partition 1082 possessing apertures 1083a and 1083b through both of which the cable is inserted, and then one end-partition is slidably drawn along the entire length of the cable. At the trunk cable's proximal end the connector protrudes slightly to enable connection to the monitor console; at the distal end the trunk cable may protrude sufficiently to allow connection of the serial cable, and the region of such connection may then be inserted inside the sheath so that the trunk cable at its distal end is fully protected by the sheath. As previously described, the distal end of the trunk cable and its mating to the proximal end of the serial cable, or the proximal end of the intermediate cable in the second configuration, are always maintained outside of the infectious zone, and this is maintained during disposition of the sheath around and over said cables.

FIG. 10B is a longitudinal section along the central axis of another configuration depicting a sheath with a compact telescopic form, which may be drawn along the entire length of the trunk cable and connections made as described above for a pleated sheath. The telescopic sheath 1090 is generally shown, with overlying folds 1091, end-partition 1092 possessing apertures 1093a and 1093b.

The apertures 1083 and 1093, if true voids in the material of the end-partition, are smaller than the diameter of the cable so that the end-partition snugly surrounds the cable and seals it from the external environment. Alternatively, the aperture may be replaced by a slit which is parted to insert the cable. End-partitions 1082 and 1092 are advantageously elastic or compliant materials to perform the function of a seal around the cable. If the material comprising the end-partition is sponge-like, it may be impregnated with an antimicrobial, which would be wiped along the cable during insertion as the end-partition is drawn along the entire length of the cable.

The sheath material may be made of any number of elastomeric materials, and may or may not incorporate an anti-microbial agent. Alternatively, the anti-microbial agent may be applied to the inner and/or outer surfaces of the sheath material.

While the two configurations of a sheath depicted herein show the sheath material in a folded manner in order to reduce the space needed to package the component, an alternative means of collapsing the sheath may be to simply bundle or bunch the material together.

Other configurations for the sheath (not shown) may consist of other means for enclosing each end of the sheath to capture it against the cable or the connector. In one configuration an adhesive material may be applied to the end of the sheath, which is then compressed against the cable or connector. Alternatively, the ends may be made with an elastic band or other cinching means which can cinch down against the cable or the connector.

Yet other configurations of the sheath may provide sufficient material to allow the sheath to extend over multiple cables of the monitoring system. In this configuration the sheath would extend into the infectious zone. It may also be made of sufficient length to reach from the monitor to the patient along the entire length of multiple cables.

While preferred configurations have been described with particularity and with reference to the drawings, modifications and variations of the foregoing will be apparent to those of skill in the art utilizing the techniques disclosed herein. It is, therefore, to be understood that such configurations are illustrative and not limiting on the scope of the present application and that the application encompasses such modifications and variations.

What is claimed is:

1. A monitoring system for transmission of information from a patient residing within an infectious zone to a monitor console using a cable assembly, said monitoring system comprising:

A monitor console to process and/or display said information from said patient; and A cable assembly comprising a trunk cable and a serial cable;

Said trunk cable being of a first length and comprising a proximal end and a distal end, said proximal end adapted to interface with said monitor console, said distal end comprising a connector, said first length defined as the distance from said proximal end to said distal end;

Said serial cable being of a second length and comprising a proximal end and a distal end, said proximal end comprising a connector, said distal end comprising at least one sensor device adapted to interface with said patient and capture said information from said patient, said second length defined as the distance from said proximal end to said distal end;

wherein said trunk cable distal end connector and said serial cable proximal end connector are each adapted to couple to one another;

wherein said cable assembly comprising said serial cable connector coupled to said trunk cable connector is configured to transmit said information from said patient to said monitor console when said sensor device is interfaced with said patient and said trunk cable is interfaced with said monitor console;

wherein said patient resides within and is surrounded by an infectious zone having an outer boundary demarcated by a perimeter located beyond the reach of any portions of said patient's body;

wherein the location of said perimeter is defined by said patient's caregiver;

wherein said monitor console resides entirely outside said perimeter of said infectious zone, said monitor console being located a distance from said perimeter, said distance being of a third length;

wherein said first length is less than said third length such that when said trunk cable proximal end is interfacing with said monitor console said trunk cable distal end connector cannot contact said perimeter of said infectious zone; and wherein the combination of said serial cable coupled to said trunk cable together has a total length equal to or greater than a distance from said sensor device interfacing with said patient to said monitor console.

2. The system of claim 1 wherein said sensor device is of a type to capture said information related to at least one of the functions of electrocardiogram, heart rate, respiration, temperature, blood pressure, bio-impedance, blood oxygen, ultrasound, electro-encephalography, pulse-oximetry and generates a signal to be transmitted along said cable assembly to said monitor.

3. The system of claim 1 wherein said serial cable is disposable.

4. The system of claim 1 wherein said serial cable and said trunk cable are electrical cables.

5. The system of claim 1 wherein said serial cable and said trunk cable are pneumatic cables and said sensor is adapted to interface with said patient's respiratory system.

6. The system of claim 1 wherein said serial cable and said trunk cable are fiber-optic cables.

7. The system of claim 1 wherein said serial cable and said trunk cable are filled with a fluid.

8. The system of claim 1 further comprising a sheath adapted to be disposed over said trunk cable and/or said serial cable;
   wherein said trunk cable and/or said serial cable are encased in said sheath.

9. The cable assembly of claim 1 wherein said at least one sensor device is adapted to couple to said serial cable distal end.

10. The cable assembly of claim 1 further comprising an intermediate cable being of a fourth length and comprising a proximal end and a distal end, said proximal end comprising a connector and said distal end comprising a connector, said fourth length defined as the distance from said proximal end to said distal end;
   wherein said intermediate cable proximal end connector and said trunk cable distal end connector are each adapted to couple to one another;
   wherein said intermediate cable distal end connector and said serial cable proximal end connector are each adapted to couple to one another;
   wherein said cable assembly comprising said serial cable coupled to said intermediate cable and said intermediate cable coupled to said trunk cable is configured to transmit said information from said patient to said monitor console when said sensor device is interfaced with said patient and said trunk cable is interfaced with said monitor console;
   wherein said second length is less than the distance from said sensor device interfacing with said patient to said trunk cable distal end connector such that said serial cable proximal end connector cannot extend to a position to be able to couple to said trunk cable distal end connector; and
   wherein the combination of said serial cable coupled to said intermediate cable and said intermediate cable coupled to said trunk cable together has a total length equal to or greater than the distance from said sensor device to said monitor console.

11. The apparatus of claim 10 wherein said second length is less than the distance from said sensor device interfacing with said patient to said perimeter such that said serial cable proximal end connector cannot extend beyond said perimeter of said infectious zone.

12. A monitoring system for transmission of electrocardiographic signals from a patient residing within an infectious zone to a monitor console using a cable assembly, said monitoring system comprising:
   A monitor console to process and/or display said signals from said patient; and
   A cable assembly comprising of a trunk cable and a serial cable;
   said trunk cable being of a first length and comprising a proximal end and a distal end, said proximal end adapted to interface with said monitor console, said distal end comprising a connector, said first length defined as the distance from said proximal end to said distal end;
   said serial cable being of a second length and comprising a proximal end and a distal end, said proximal end comprising a connector, said distal end comprising at least one electrode adapted to interface with said patient and capture said electrocardiographic signals from said patient, said second length defined as the distance from said proximal end to said distal end;
   wherein said trunk cable distal end connector and said serial cable proximal end connector are each adapted to couple to one another;
   wherein said cable assembly comprising said serial cable connector coupled to said trunk cable connector is configured to transmit said electrocardiographic signals from said patient to said monitor console when said electrode is interfaced with said patient and said trunk cable is interfaced with said monitor console;
   wherein said patient resides within and is surrounded by an infectious zone having an outer boundary demarcated by a perimeter located beyond the reach of any portions of said patient's body;
   wherein the location of said perimeter is defined by said patient's caregiver;
   wherein said monitor console resides entirely outside said perimeter of said infectious zone, said monitor console being located a distance from said perimeter, said distance being of a third length;
   wherein said first length is less than said third length such that when said trunk cable proximal end is interfacing with said monitor console said trunk cable distal end connector cannot contact said perimeter of said infectious zone; and
   wherein the combination of said serial cable coupled to said trunk cable together has a total length equal to or greater than a distance from said electrode interfacing with said patient to said monitor console.

13. The cable assembly of claim 12 further comprising an intermediate cable being of a fourth length and comprising a proximal end and a distal end, said proximal end comprising a connector and said distal end comprising a connector, said fourth length defined as the distance from said proximal end to said distal end;
   wherein said intermediate cable proximal end connector and said trunk cable distal end connector are each adapted to couple to one another;
   wherein said intermediate cable distal end connector and said serial cable proximal end connector are each adapted to couple to one another;
   wherein said cable assembly comprising said serial cable coupled to said intermediate cable and said intermediate cable coupled to said trunk cable is configured to transmit said electrocardiographic signals from said patient to said monitor console when said electrode is interfaced with said patient and said trunk cable is interfaced with said monitor console;
   wherein said second length is less than the distance from said electrode interfacing with said patient to said trunk cable distal end connector such that said serial cable proximal end connector cannot extend to a position to be able to couple to said trunk cable distal end connector, and
   wherein the combination of said serial cable coupled to said intermediate cable and said intermediate cable coupled to said trunk cable together has a total length equal to or greater than the distance from said electrode interfacing with said patient to said monitor console.

14. The apparatus of claim 13 wherein said second length is less than the distance from said electrode interfacing with said patient to said perimeter such that said serial cable proximal end connector cannot extend beyond said perimeter of said infectious zone.

15. The cable assembly of claim 12 wherein said at least one electrode is adapted to couple to said serial cable distal end.

16. A method of preventing the transfer of infective agents along a series of patients utilizing a monitoring system, said monitoring system to be subsequently used consecutively amongst said series of patients, comprising:
  Defining an infectious zone surrounding said patient that is contaminated with infective agents, said infectious zone having an outer boundary demarcated by a perimeter located beyond the reach of any portions of said patient's body and where the location of said perimeter is defined by said patient's caregiver;
  Deploying a monitor console configured to process and/or display information conveyed from said patient, and placing said monitor console outside of said perimeter of said infectious zone such that it resides a distance from said perimeter, said distance defined by a third length;
  Deploying a cable assembly comprising a trunk cable and a serial cable,
  said trunk cable being of a first length and comprising a proximal end adapted to interface with said monitor console and a distal end comprising a connector, said first length defined as the distance from said proximal end to said distal end,
  said serial cable being of a second length and comprising a proximal end and a distal end, said proximal end comprising a connector and a said distal end comprising a sensor device adapted to interface with said patient, said second length defined as the distance from said proximal end to said distal end,
  said trunk cable distal end connector and said serial cable proximal end connector adapted to couple to one another;
  wherein said first length is less than said third length such that when said trunk cable proximal end is interfacing with said monitor console, said trunk cable distal end connector cannot contact said perimeter of said infectious zone, and
  wherein the combination of said serial cable coupled to said trunk cable together has a total length equal to or greater than a distance from said sensor device interfacing with said patient to said monitor console;
  Connecting said patient to said monitor console through said cable assembly;
  wherein said connecting said patient comprises the steps of:
  (1) Interfacing said trunk cable proximal end to said monitor console and placing the entirety of said trunk cable in a position outside said perimeter of said infectious zone;
  (2) Coupling said trunk cable distal end connector to said serial cable proximal end connector such that both connectors are positioned outside said perimeter of said infectious zone;
  (3) Extending said serial cable distal end into said infectious zone to reach said patient; and
  (4) Interfacing said sensor device to said patient so that information can be acquired from said patient and transmitted to said monitor console;
  Monitoring said patient for a period of time;
  Disconnecting said patient from said monitor console by decoupling said serial cable proximal end connector from said trunk cable distal end connector while maintaining the trunk cable outside said perimeter of said infectious zone, thereby keeping said trunk cable and said monitor console free from contamination and preventing said transfer of said infective agents to a subsequent patient in said series of patients.

17. The method of claim 16 further comprising a sheath adapted to be disposed over a said trunk cable such that said trunk cable is encased in said sheath, wherein said step of connecting said patient to said monitor further comprises the step of disposing said sheath over said trunk cable.

18. The method of claim 17 wherein said sheath has a length greater than said trunk cable and said step of disposing said sheath over said trunk cable further comprises extending said sheath distally over a portion of said serial cable.

19. A monitoring system for transmission of information from a patient residing within an infectious zone to a monitor console using a cable assembly, said monitoring system comprising:
  A monitor console to process and/or display said information from said patient; and
  A cable assembly comprising a trunk cable, an intermediate cable, and a serial cable;
  said trunk cable being of a first length and comprising a proximal end and a distal end, said proximal end adapted to interface with said monitor console, said distal end comprising a connector, said first length defined as the distance from said proximal end to said distal end;
  said intermediate cable being of a second length and comprising a proximal end and a distal end, said proximal end comprising a connector and said distal end comprising a connector, said second length defined as the distance from said proximal end to said distal end; and
  said serial cable being of a third length and comprising a proximal end and a distal end, said proximal end comprising a connector, said distal end comprising at least one sensor device adapted to interface with said patient and capture said information from said patient, said third length defined as the distance from said proximal end to said distal end;
  wherein said trunk cable distal end connector and said intermediate cable proximal end connector are each adapted to couple to one another;
  wherein said intermediate cable distal end connector and said serial cable proximal end connector are each adapted to couple to one another;
  wherein said cable assembly comprising said serial cable coupled to said intermediate cable and said intermediate cable coupled to said trunk cable is configured to transmit said information from said patient to said monitor console when said sensor device is interfaced with said patient and said trunk cable is interfaced with said monitor console;
  wherein said patient resides within and is surrounded by an infectious zone having an outer boundary demarcated by a perimeter located beyond the reach of any portions of said patient's body;
  wherein the location of said perimeter is defined by said patient's caregiver;
  wherein said monitor console resides entirely outside of said perimeter, said monitor console being located a distance from said perimeter, said distance being of a fourth length;
  wherein said first length is less than said fourth length such that when said trunk cable proximal end is interfacing with said monitor console said trunk cable distal end connector cannot contact said perimeter of said infectious zone;

wherein said third length is less than the distance from said sensor device interfacing with said patient to said trunk cable distal end connector such that said serial cable proximal end connector cannot extend to a position to be able to couple to said trunk cable distal end connector; and wherein the combination of said serial cable coupled to said intermediate cable and said intermediate cable coupled to said trunk cable together has a total length equal to or greater than a distance from said sensor device interfacing with said patient to said monitor console.

20. The cable assembly of claim 19 wherein said at least one sensor device is adapted to couple to said serial cable distal end.

21. The system of claim 19 further comprising a sheath adapted to be disposed over a said trunk cable and/or said intermediate cable and/or said serial cable;

wherein said trunk cable and/or said intermediate cable and/or said serial cable are encased in said sheath.

22. The apparatus of claim 19 wherein said third length is less than the distance from said sensor device interfacing with said patient to said perimeter such that said serial cable proximal end connector cannot extend beyond said perimeter of said infectious zone.

23. A method of preventing the transfer of infective agents along a series of patients utilizing monitoring system, said monitoring system to be subsequently used consecutively amongst said series of patients, comprising:

Defining an infectious zone surrounding said patient that is contaminated with infective agents, said infectious zone having an outer boundary demarcated by a perimeter located beyond the reach of any portions of said patient's body and where the location of said perimeter is defined by said patient's caregiver;

Deploying a monitor console configured to process and/or display information conveyed from said patient, and placing said monitor console outside of said perimeter of said infectious zone such that it resides a distance from said perimeter, said distance defined by a fourth length;

Deploying a cable assembly comprising a trunk cable, an intermediate cable, and a serial cable, said trunk cable being of a first length and comprising a proximal end adapted to interface with said monitor console and a distal end comprising a connector, said first length defined as the distance from said proximal end to said distal end, said intermediate cable being of a second length and comprising a proximal end and a distal end, said proximal end comprising a connector and said distal end comprising a connector, said second length defined as the distance from said proximal end to said distal end;

said serial cable being of a third length and comprising a proximal end and a distal end, said proximal end comprising a connector and said distal end comprising at least one sensor device adapted to interface with said patient, said third length defined as the distance from said proximal end to said distal end;

said trunk cable distal end connector and said intermediate cable proximal end connector adapted to couple to one another; and said intermediate cable distal end connector and said serial cable proximal end connector adapted to couple to one another;

wherein said first length is less than said fourth length such that when said trunk cable proximal end is interfacing with said monitor console, said trunk cable distal end connector cannot contact said perimeter of said infectious zone; and wherein the combination of said serial cable coupled to said intermediate cable and said intermediate cable coupled to said trunk cable together has a total length equal to or greater than a distance from said sensor device interfacing with said patient to said monitor console;

Connecting said patient to said monitor console through said cable assembly;

wherein said connecting said patient comprises the steps of:
(1) Interfacing said trunk cable proximal end to said monitor console and placing the entirety of said trunk cable in a position outside said perimeter of said infectious zone;
(2) Coupling said trunk cable distal end connector to said intermediate cable proximal end connector such that both connectors are positioned outside said perimeter of said infectious zone;
(3) Interfacing said sensor device with said patient; and
(4) Extending said intermediate cable distal end towards said patient and coupling it to said serial cable proximal end connector such that said patient is connected to said monitor console so that information can be acquired from said patient and transmitted to said monitor console;

Monitoring said patient for a period of time;

Disconnecting said patient from said monitor console by decoupling said intermediate cable proximal end connector from said trunk cable distal end connector while maintaining said trunk cable outside said perimeter of said infectious zone, thereby keeping said trunk cable and said monitor console free from contamination and preventing said transfer of said infective agents to a subsequent patient in said series of patients.

24. The method of claim 23 further comprising a sheath adapted to be disposed over said trunk cable and/or said intermediate cable such that said trunk cable and/or said intermediate cable is encased in said sheath, wherein said step of connecting said patient to said monitor further comprises the step of disposing said sheath over said trunk cable and/or said intermediate cable.

25. The method of claim 23 wherein said third length is less than the distance from said sensor device interfacing with said patient to said perimeter such that said serial cable proximal end connector cannot extend beyond said perimeter of said infectious zone.

* * * * *